US008864710B2

(12) United States Patent
Akahoshi

(10) Patent No.: US 8,864,710 B2
(45) Date of Patent: Oct. 21, 2014

(54) INFUSION SLEEVE WITH DISTENDABLE PORT

(75) Inventor: Takayuki Akahoshi, Tokyo (JP)

(73) Assignee: Art, Limited, Grand Cayman (KY)

( * ) Notice: Subject to any disclaimer, the term of this patent is extended or adjusted under 35 U.S.C. 154(b) by 395 days.

(21) Appl. No.: 12/856,358

(22) Filed: Aug. 13, 2010

(65) Prior Publication Data
US 2011/0172590 A1 Jul. 14, 2011

Related U.S. Application Data

(60) Provisional application No. 61/293,399, filed on Jan. 8, 2010, provisional application No. 61/293,389, filed on Jan. 8, 2010.

(51) Int. Cl.
A61M 1/00 (2006.01)
A61M 5/178 (2006.01)
A61F 9/007 (2006.01)

(52) U.S. Cl.
CPC .................. A61F 9/00745 (2013.01)
USPC ..................... 604/119; 604/167.04

(58) Field of Classification Search
USPC ............... 604/27, 30, 31, 35, 118, 119, 129, 604/167.01, 167.02, 167.03, 167.04, 246, 604/247, 256, 264, 28
See application file for complete search history.

(56) References Cited

U.S. PATENT DOCUMENTS

| 5,151,084 A | * | 9/1992 | Khek | 604/22 |
| 5,776,096 A | * | 7/1998 | Fields | 604/43 |
| 2002/0165492 A1 | * | 11/2002 | Davey et al. | 604/167.04 |
| 2010/0160851 A1 | * | 6/2010 | Dimalanta et al. | 604/22 |

* cited by examiner

Primary Examiner — Aarti B Berdichevsky
Assistant Examiner — Bradley Osinski
(74) Attorney, Agent, or Firm — Wood, Phillips, Katz, Clark & Mortimer

(57) ABSTRACT

An infusion sleeve for use with a phacoemulsification needle has a hollow body with an open end by which the sleeve is attachable to a handpiece and an open tip through which a phacoemulsification needle is passed. Irrigating liquid is directed from the handpiece through the sleeve. At least one discharge ports is formed in the sleeve to provide increased flow of irrigating liquid into the eye. The port or ports may differ in size, shape and positioning on the sleeve. At least one such port has a slit extending therefrom cutting through the sleeve and adapted to distend or open up under certain flow conditions, effectively increasing the cross-sectional area of the port available for flow. When flow conditions return to normal the slit returns to its "closed" position. Another such port is formed as a flap which opens and closes responsive to the flow of the irrigating liquid.

5 Claims, 4 Drawing Sheets

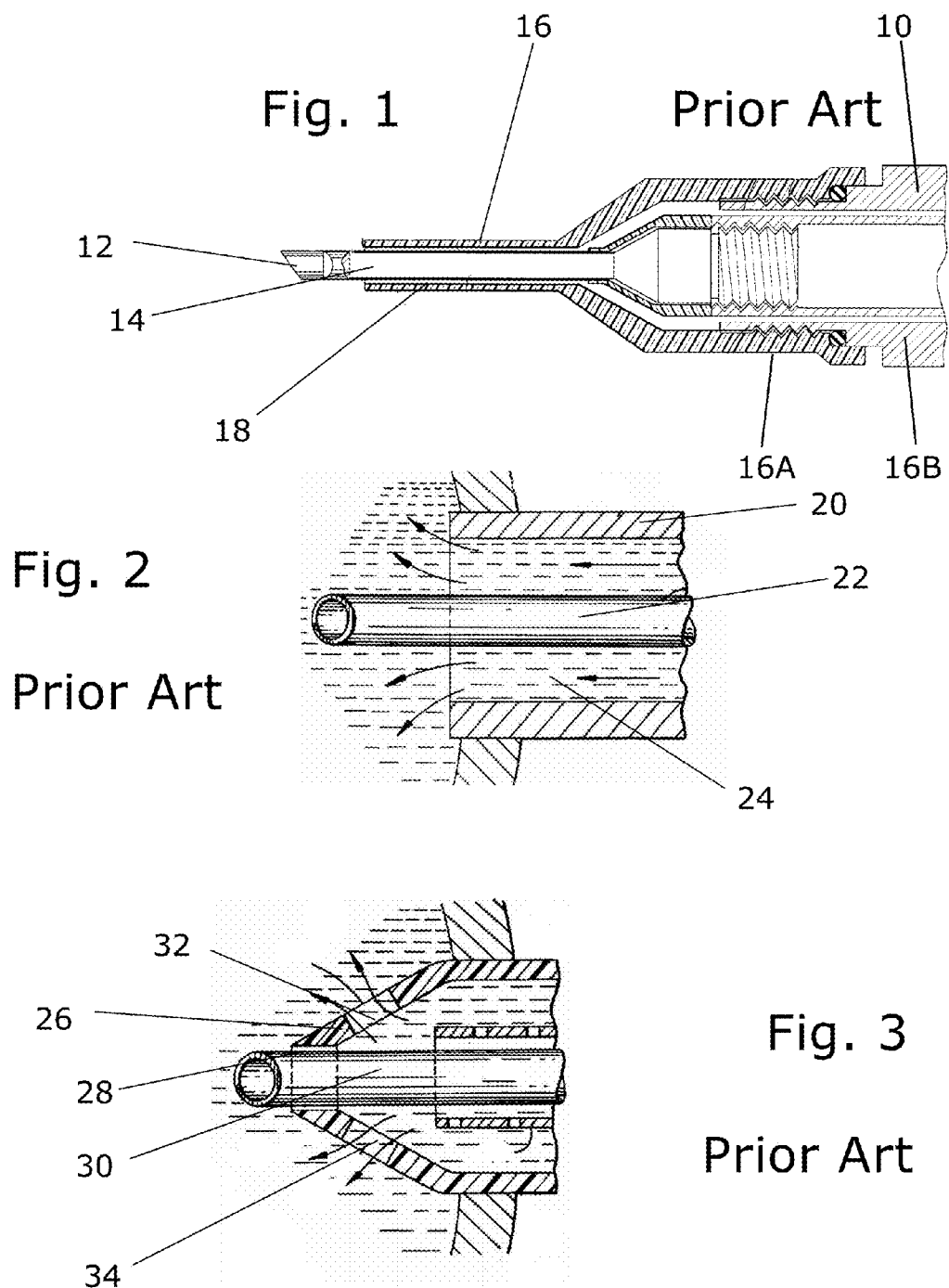

INFUSION SLEEVE WITH DISTENDABLE PORT

This application claims priority from U.S. patent application Ser. No. 61/293,389, filed 8 Jan. 2010 and entitled "Infusion Sleeve with Flow Control" and U.S. patent application Ser. No. 61/293,399 filed 8 Jan. 2010 and entitled "Infusion Sleeve With Distendable Port", both of which are incorporated herein by reference.

This invention relates to surgical instruments and surgical techniques used in eye surgery and more particularly, to the technique of phacoemulsification apparatus and methods for their use.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such technique is known as phacoemulsification. A typical phacoemulsification tool includes a hollow needle to which electrical energy is applied to vibrate the needle at ultrasonic frequencies in order to fragment the diseased lens into small enough particles to be aspirated from the eye. Commonly, an infusion sleeve is mounted around the needle to supply irrigating liquids to the eye in order to aid in flushing and aspirating the lens particles and cortical material through an aspiration port formed in the hollow needle.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such a collapse and this damage is permanent because these cells do not regenerate. One of the benefits of using as small an incision as possible during such surgery is the minimization of leakage during and after surgery which aids in the prevention of such a collapse.

One way to ensure infusion of a sufficient amount of liquid into the eye during an operation is to regulate the flow of irrigating liquid through the sleeve. For example, during phacoemulsification the aspiration port on the phaco needle can become occluded with lens fragments or particles. If the sleeve is of the type having an infusion port at its tip, surrounding the needle, it may also become occluded. When this happens, flow of irrigating liquid into the eye may decrease, meaning that not enough liquid flow may be available to help clear the occlusion. If the surgeon acts to increase liquid flow through the infusion sleeve. This can cause an increase in the Reynolds number of the infusion liquid to the point where the liquid flow become turbulent which can, in itself cause damage to the eye.

Flow control may also be desirable for sleeves having discharge ports that direct the liquid toward the needle tip may create a flow pattern that pushes lens or cortical material away from the aspiration port of the needle, prolonging the phaco procedure.

Instruments using various types of infusing sleeves are well known and well-represented in the art and exemplify the attempts made by others to address the problem of maintaining an adequate flow of irrigating liquid without causing damage to the eye.

U.S. Pat. No. 4,643,717 (Cook et al) teaches and describes an aspiration fitting adapter formed as a sleeve concentric to the phaco needle and having a pair of bilaterally opposed discharge ports formed proximate the end of the sleeve to infuse irrigating liquid into the eye.

U.S. Pat. No. 5,151,084 (Khek) teaches and describes an ultrasonic needle with an infusion sleeve that includes a baffle. The sleeve of Khek also fits concentrically about the needle and allows the needle to protrude a substantial distance therefrom while providing pair of discharge ports bilaterally opposed to each other near the terminus of the sleeve.

U.S. Pat. No. 6,117,151 (Urich et al) teaches and describes an eye incision temperature protection sleeve fitted concentrically about a needle and having a single discharge port through which irrigating liquid is passed.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

A series of patents issued to Richard J. Mackool illustrates further variations of irrigating sleeves. Mackool forms the sleeve with a somewhat flattened cross-section configuration intended to more closely approximate the shape of the incision through which the sleeve is inserted into the eye. This cross-section can be seen at FIG. 3 of U.S. Pat. No. 5,084,009.

U.S. Pat. No. 5,084,009 (Mackool) teaches and describes a liquid infusion sleeve for use during eye surgery with the sleeve having a flattened cross-section and having a pair of infusion ports formed on the forward portion of the flattened section.

U.S. Pat. No. 5,286,256 (Mackool) teaches and describes a liquid infusion sleeve having a free-floating rigid sleeve surrounding a needle which is intended to prevent the outer flexible sleeve from collapsing onto the needle.

U.S. Pat. No. 5,354,265 (Mackool) teaches and describes a liquid infusion sleeve showing yet another construction intended to keep the outer flexible infusion sleeve from collapsing onto the vibrating needle.

U.S. Pat. No. 5,505,693 (Mackool) teaches and describes a method and apparatus for reducing friction and heat generation by an ultrasonic device during surgery incorporating a needle support to prevent collapse of the outer flexible sleeve.

The Mackool patents are characterized by a pair of discharge ports formed at the distal end of the sleeve through which irrigating liquid is passed into the eye during the operation.

U.S. Pat. No. 5,645,530 (Boukhny) teaches and describes a phaco emulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

U.S. Pat. No. 5,634,912 (Injev) teaches and describes an infusion sleeve having a rotating tip to allow the phaco needle to be repositioned during surgery. The top also has a single discharge port for infusing liquid during surgery.

Published U.S. Patent Application 2003/0004455 (Kadziauskas) teaches and describes a bi-manual phaco needle using separate emulsification and aspiration needles inserted into the eye simultaneously during surgery.

U.S. Pat. No. 6,007,555 (Devine) teaches and describes an ultrasonic needle for surgical emulsification and details the tendency of some ultrasonic phaco needles to force lens fragments away from the needle's aspiration port.

U.S. Pat. Nos. 6,299,591, 6,159,175, 5,743,871, 5,741,226 and 5,725,495 (Banko) all teach and describe a phacoemulsification handpiece, sleeve and tip, with the sleeve having permanently fixed exterior and/or internal baffles thereon to direct the flow of irrigation fluid away from the needle's aspiration port. The external baffles effectively increase the diameter of the sleeve while the internal baffles are relatively difficult or expensive to manufacture as compared to an extruded sleeve.

U.S. Pat. No. 7,601,135 (Akahoshi) teaches and describes a multi-port infusion sleeve with ports formed on the curved portion of the sleeve proximate the end thereof.

U.S. Pat. No. 7,601,136 (Akahoshi) teaches and describes an infusion sleeve with ports formed on the curved portion of the sleeve proximate the end thereof.

The need exists for an improved infusion sleeve which allows for a greater volume of liquid to be infused into the eye while avoiding the problems described in the prior art with respect to pushing lens and cortical material away from the aspiration port or damaging delicate eye tissue impacted by such direct flow due to increased pressure, turbulence and the like.

The need also exists for such improved infusion sleeves to incorporate a flow-directing expedient that does not extend above the surface of the sleeve during insertion and removal of the phaco needle through the incision.

The need also exists for such improved infusion sleeves to be simple in construction, efficient in operation and economical to manufacture.

In accordance with a first preferred embodiment of the present invention, a phaco infusion sleeve has at least one infusion liquid discharge port thereon formed by severing a portion of the sleeve to create a flap which, responsive to an increase in the flow of the irrigation liquid, swings out to direct the liquid in a desired direction. One such configuration directs the liquid flow away from the needle tip to limit the extent to which lens and cortical material are pushed away from the phaco needle.

In accordance with another preferred embodiment of the present invention, a phaco infusion sleeve has at least one infusion liquid discharge port on the lateral part of the sleeve. The port has at least one slit beginning at the periphery of the port and extending a selected distance away from the port. Under normal flow conditions the slit remains closed and the flow of liquid is directed through the undistended port. When an occlusion of the aspiration port occurs and increased pressure in the eye causes the flow of infusion liquid to back up the slit is forced open, increasing the cross-sectional area of the port available for liquid flow allowing a larger volume of liquid to enter the eye more safely.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further aspects of the present invention will become apparent upon consideration of the accompanying drawing figures in which:

BRIEF DESCRIPTION OF THE DRAWINGS

FIG. 1 is a first prior art illustration of a prior art irrigation sleeve;

FIG. 2 is a second illustration of a prior art irrigation sleeve;

FIG. 3 is a third illustration of a prior art irrigation sleeve;

DETAILED DESCRIPTION OF THE DRAWINGS

Figure 4:
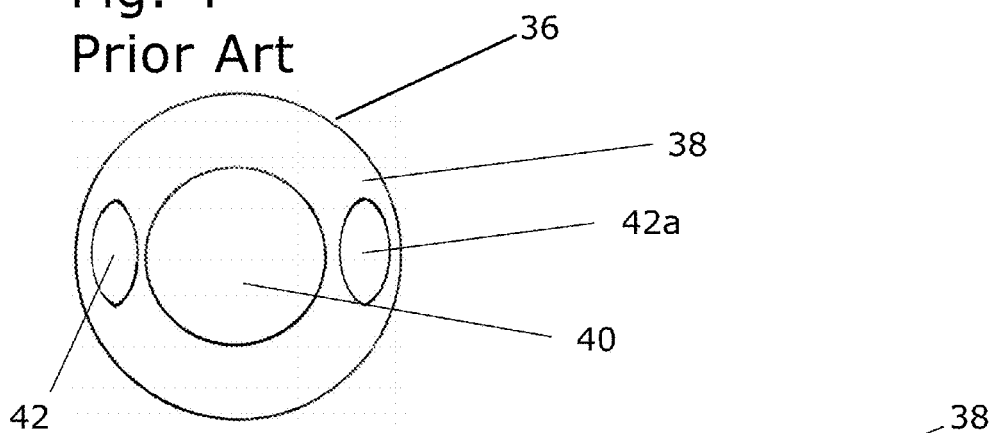
FIG. 4 is an end view of a prior art irrigation sleeve having two circular and bilaterally opposed discharge ports.

Referring now to FIG. 1 the numeral 10 indicates generally a partial sectional view of a prior art phacoemulsification hand piece having a needle 12 defining a hollow internal chamber 14 through which irrigation liquid and emulsified particles of a lens are aspirated from the capsular bag. As seen in FIG. 1, an irrigating sleeve 16 is mounted to hand piece 10, from which needle 12 protrudes. Sleeve 16 communicates with an irrigation liquid supply within handpiece 10 and provides irrigating liquid to the capsular bag through an annular channel 18 formed between needle 12 and sleeve 16.

Referring now to FIG. 2, an enlarged partial sectional view of a second prior art phacoemulsification apparatus is shown having a sleeve 20 surrounding a hollow needle 22 and defining therebetween an annular channel 24 as a conduit for irrigating liquid.

Both FIG. 1 and FIG. 2 show a prior art apparatus with the flow of irrigating liquid directed annularly about the periphery of the hollow phaco needle.

Referring now to FIG. 3, a partial sectional view of a second embodiment of the apparatus of FIG. 2 is shown where the infusion sleeve 26 tapers to form an opening 28 through which needle 30 extends. A pair of infusion ports 32, 34 are formed in the angled side walls of sleeve 26 to form a pathway for infusing liquid.

The embodiments shown in FIGS. 2 and 3 are taken from U.S. Pat. No. 5,084,009 and as discussed above, it appears that ports 32, 34 are formed along the flattened portion of sleeve 26 and are the only infusion ports present.

Figure 5:
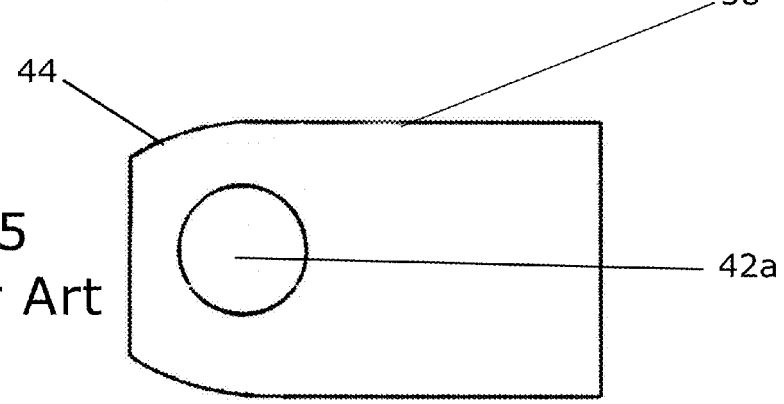
FIG. 5 is a lateral view of a portion of the sleeve shown in FIG. 4.
Figure 6:
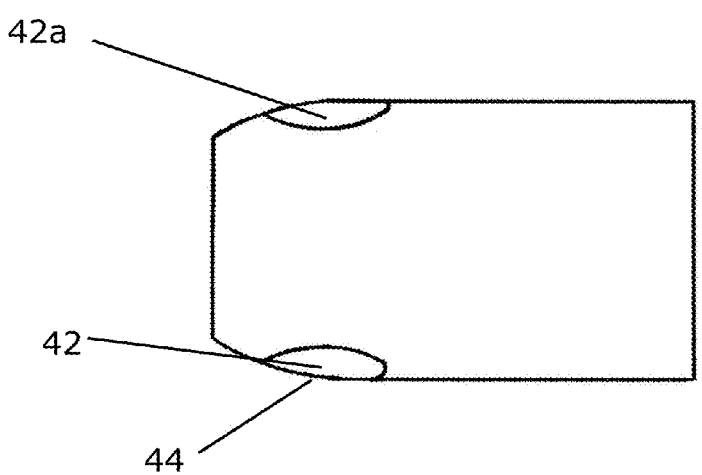
FIG. 6 is a top view of a portion of the sleeve shown in FIG. 4.

FIGS. 4-6 demonstrate a prior art phaco infusion sleeve. For purposes of clarity, only the tip portion of each such sleeve will be shown, it being understood that the sleeve is fitted coaxial to a phaco needle which extends outward from the sleeve.

FIG. 4 is an end view of a known prior art infusion sleeve 36 having an outer sleeve wall 38, a central passage 40 to accommodate the phaco needle and a pair of diametrically opposed infusion ports 42, 42a. This is the present arrangement on a currently available infusion sleeve.

FIG. 5 is a lateral side view of the sleeve tip shown in FIG. 4, demonstrating that the infusion ports 42, 42a are circular in shape. FIG. 6 is a top view of the tip of FIG. 4 again demonstrating the diametrically opposed positions of infusion ports 42, 42a are positioned on taper 44.

Figure 7:
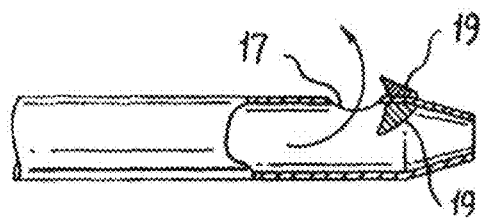
FIG. 7 is a detail view of a prior art sleeve showing interior and exterior baffles.

Referring to FIG. 7, a detail of a prior art phaco sleeve is shown, corresponding to FIG. 3G of U.S. Pat. No. 6,299,591. Using the numerals in the original drawing, a phaco sleeve is shown having an irrigation port 17 through which irrigating liquid passes. Also seen in FIG. 7 are baffles 19, shown formed on both the interior and exterior of the sleeve. According to the patentee, baffles 19 redirect the flow of irrigating liquid in the direction of the arrow which, in this case, is a direction away from the aspiration port formed at the distal end of the phaco needle (not shown in this illustration). It is apparent that the exterior baffle 19 effectively increases the diameter of the sleeve and must be compressed, bent or otherwise distended to fit through a typical incision made for phaco purposes.

Figure 8:
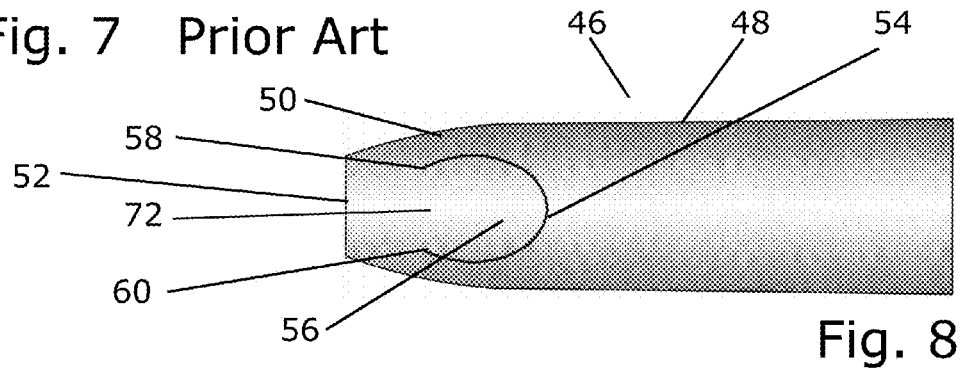
FIG. 8 is a lateral view of a sleeve embodying the present invention.

Referring now to FIG. 8 the numeral 46 identifies a portion of a phaco sleeve having a body 48 and a tip portion 50 which tapers to a distal end 52. Sleeve 48 is of the type having a central passageway for aspiration liquid flow which extends to end 52, with the central passageway shaped and dimensioned to fit around the periphery of a phaco needle and allow the end of the needle to extend past the end 52.

In the embodiment shown in FIG. 8 a portion of sleeve 46 is cut to form a generally U-shaped or horseshoe-shaped slit 54 to form a flap 56. Slit 54 terminates at slit ends 58, 60 which, in this embodiment, are intermediate flap 56 and end 52.

Figure 9:
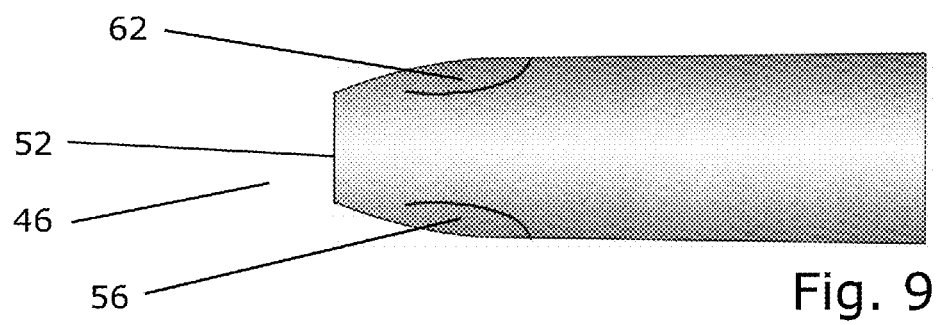
FIG. 9 is a top view of the sleeve of FIG. 8.

Referring now to FIG. 9, sleeve 46 is shown in a top view, showing the formation of a second flap, 62, formed in the same fashion as flap 56. Although flaps 56 and 62 are shown formed to be diametrically opposed to each other on sleeve 46 it should be understood that different numbers of flaps can be formed on sleeve 46 to create or modify flow patterns as desired. In like fashion, the size and positioning of flaps such as 56 can also be changed to create different flow patterns.

Figure 10:
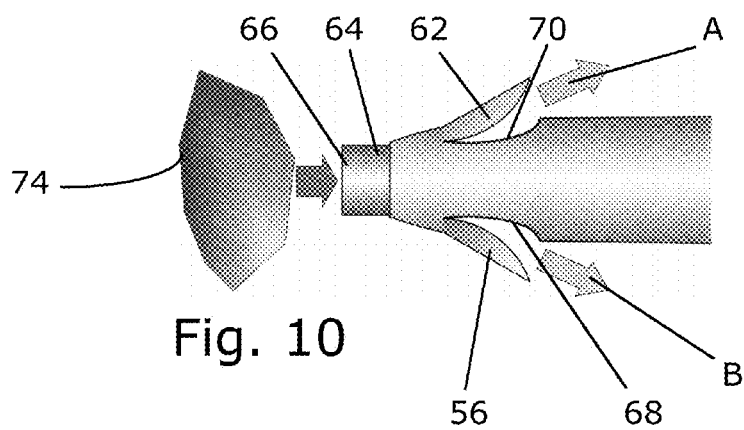
FIG. 10 is a view of the sleeve of FIG. 9 with infusing liquid passing therethrough.

Referring now to FIG. 10 the operation of sleeve 46 can now be described. In FIG. 10, sleeve 46 is seen mounted concentrically to a hollow phaco needle 64 which, as is typical, terminates in an aspiration port 66 through which lens and cortical material are passed. Sleeve 46 fits sufficiently liquid-tightly to needle 64 to force irrigating liquid passing through sleeve 46 at flaps 56, 62 to force flaps 56, 62 outward and away from sleeve body 48, creating infusion ports 68, 70 and directing liquid passing therethrough to flow in directions A and B which, in this embodiment, are in a direction away from aspiration port 66. In effect, as seen in FIG. 8, the portion of sleeve 46 extending between slit end points 58, 60 forms a living hinge 72 which allows flap 56 to swing away from body 48 responsive to the flow of liquid passing through sleeve 46. It is expected that as the flow increases, flaps 56, 62 will swing farther away from body 48, thus reducing the resistance to flow through irrigation ports 68, 70.

The effect on phacoemulsification created by flaps 56, 62 is seen in FIG. 10 where, when liquid is aspirated through needle port 66, particle 74 is drawn toward aspiration port 66 without being impeded or repulsed by the flow of irrigating liquid into the eye.

While the embodiment shown in FIGS. 8-10 is intended to direct liquid flow away from aspiration port 66 it should readily be understood that the manner in which slit 54 is cut can change the flow direction. For example, if slit 54 were cut to place end points 58, 60 toward the proximal end of sleeve 46, flap 58 would open in a fashion which would direct irrigating liquid in a forward direction, toward aspiration port 66, should such a flow pattern be deemed useful. Different flow patterns can also be achieved if flap 56 is formed in a different geometric shape, such as a square, rectangle, triangle or the like.

Figure 11:
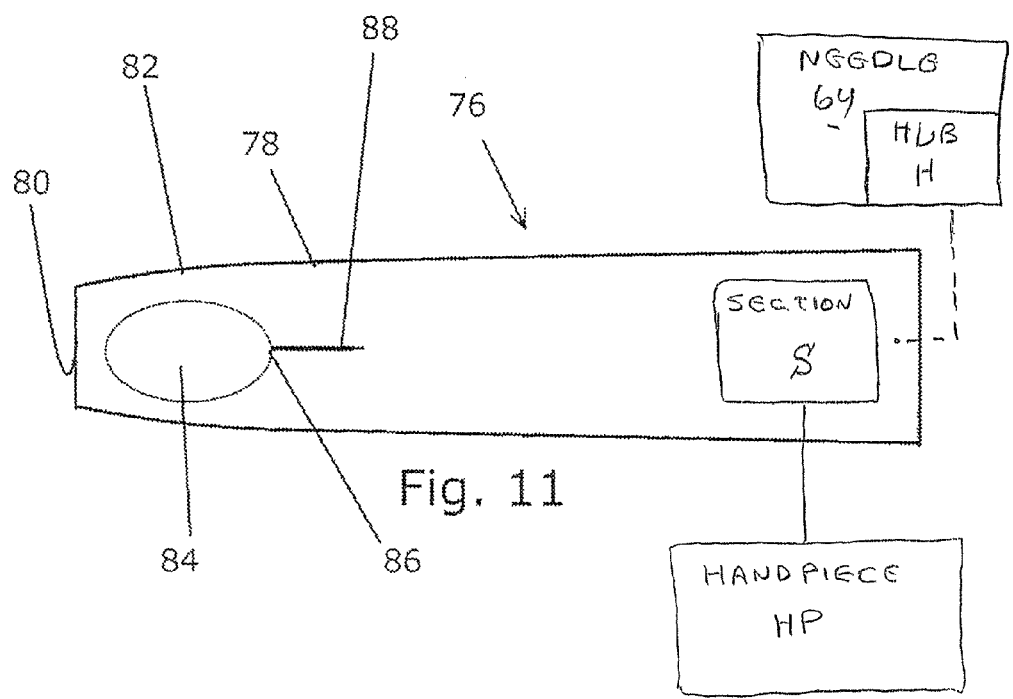
FIG. 11 is a lateral view of a sleeve embodying an embodiment of the present invention.

Referring now to FIG. 11 a phaco sleeve 76 is shown having a tip 78 terminating at an open sleeve end 80. A curved or tapered shoulder 82 extends from end 80. The depiction of sleeve 76 is for illustrative purposes, understanding that such sleeves are available in a number of different sizes and configurations.

A section S on the proximal end of the tubular body is configured to surround a hub H on the phacoemulsification needle 64 and for connection to a phacoemulsification handpiece HP.

A lateral infusion port 84 is shown on sleeve 76 as described generally above. The depiction of port 84 is illustrative only, recognizing the number of varied sizes and shapes of such ports known in the prior art. At point 86 of port 84's perimeter a slit 88 is formed extending laterally along and through sleeve 86, beginning at and communicating with port 84. In other words, port 84 is an opening extending through sleeve 76, and slit 88 likewise extends through sleeve 76 and connects with port 84.

FIG. 11 represents sleeve 48 in a first state under normal flow conditions with no occlusions of either the sleeve or the needle's aspiration port. Under such circumstances, slit 88 remains closed or undistended and little or no infusion liquid passes therethrough.

Figure 12:
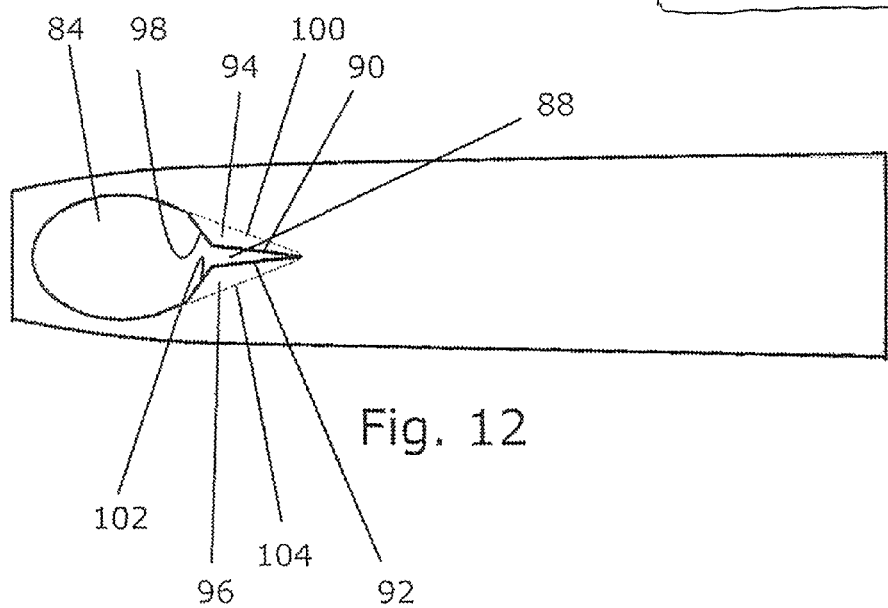
FIG. 12 is lateral view of the sleeve of FIG. 11 showing the discharge port distended to allow increased liquid flow.

Referring now to FIG. 12, port 84 is shown as it would appear when occlusion is taking place and with the sleeve 48 in a second state. Slit edges 90, 92 have been pushed or folded outward by the force of the infusion liquid flow, forming flaps 94, 96. In this illustration, flap 94 comprises a generally triangular flap defined by slit edge 90, contiguous port rim segment 98 and "fold line" 100. Similarly, flap 96 is defined by slit edge 92, contiguous port rim portion 102 and "fold line" 104.

It should be apparent that the shape and size of flaps 94, 96 will vary with the shape and size of port 84 and the length of slit 88. All of these parameters can be selected to result in a sleeve port that will allow a determinable change in flow characteristics to meet the demands of a particular sleeve configuration or phaco needle apparatus. In any such configuration the distension or "folding out" of flaps 94, 96 creates a larger cross-section available for infusion liquid flow when occlusion or other changes in flow occur. When the flow returns to normal, flaps 94, 96 return to their "closed" position and port 84 returns to its original configuration and size.

What is claimed is:

1. A method of performing phacoemulsification, the method comprising the steps of:
providing an infusion sleeve with a hollow body having an open end, a port extending through the infusion sleeve and having a first cross-section bounded by a rim, and a slit through the infusion sleeve beginning at and in communication with the port and bounded by first and second edges, the infusion sleeve having a first state with no flow of infusion liquid through the infusion sleeve body to and through the open end;

directing infusion liquid into the infusion sleeve hollow body with the open end occluded as an incident of which the infusion sleeve is changed from the first state into a second state wherein a flap is folded out of the infusion sleeve about a fold line to create an additional cross-section, contiguous with the first cross-section, for infusion liquid flowing from the infusion sleeve body, the flap bounded by a segment of the rim, the first slit edge, and the fold line; and directing infusion liquid into the infusion sleeve body without the open end occluded with the infusion sleeve in the first state wherein the flap is not folded out of the infusion sleeve.

2. The method of performing phacoemulsification according to claim 1 wherein the hollow body has a tubular section to surround a portion of a shaft of a phacoemulsification needle, the tubular body section having a proximal end and a distal end, and an inner surface and an outer surface, a section is formed on the proximal end of the tubular body section and is configured to surround a hub of said phacoemulsification needle and for connection to a phacoemulsification handpiece.

3. The method of performing phacoemulsification according to claim 2 wherein the slit is a linear slit oriented longitudinally on the tubular body section.

4. The method of performing phacoemulsification according to claim 2 wherein the tubular body has a tip portion that tapers to the distal end of the tubular body section.

5. The method of performing phacoemulsification according to claim 1 wherein as an incident of directing infusion liquid into the infusion sleeve hollow body with the open end occluded, a second flap is folded out of the infusion sleeve about a second fold line.

* * * * *